United States Patent [19]

Young

[11] Patent Number: 4,582,694

[45] Date of Patent: * Apr. 15, 1986

[54] SHOCK CALCINED CRYSTALLINE SILICA CATALYSTS

[75] Inventor: Dean A. Young, Yorba Linda, Calif.

[73] Assignee: Union Oil Company of California, Los Angeles, Calif.

[*] Notice: The portion of the term of this patent subsequent to Apr. 8, 2003 has been disclaimed.

[21] Appl. No.: 623,180

[22] Filed: Jun. 21, 1984

[51] Int. Cl.$^4$ .............................................. C01B 33/12
[52] U.S. Cl. ..................................... 423/335; 502/85; 585/467
[58] Field of Search .......................... 423/335; 502/85; 585/467

[56] References Cited

U.S. PATENT DOCUMENTS

| | | | |
|---|---|---|---|
| 3,528,615 | 9/1970 | Kokotailo | 502/85 |
| 3,766,056 | 10/1973 | Young | 585/467 |
| 3,941,871 | 3/1976 | Dwyer et al. | 423/328 |
| 4,016,218 | 4/1977 | Haag et al. | 585/467 |
| 4,061,724 | 12/1977 | Grose et al. | 423/339 |
| 4,073,865 | 2/1978 | Flanigen et al. | 423/339 |
| 4,104,294 | 8/1978 | Grose et el. | 502/62 |
| 4,234,549 | 11/1980 | Stanley et al. | 423/245 |
| 4,276,017 | 5/1981 | Young | 502/214 |
| 4,283,306 | 8/1981 | Herkes | 502/202 |
| 4,309,275 | 1/1982 | Mulaskey | 208/109 |
| 4,309,276 | 1/1982 | Miller | 208/109 |
| 4,325,929 | 4/1982 | Young | 423/339 |
| 4,344,927 | 8/1982 | Young | 423/335 |
| 4,362,653 | 12/1982 | Robinson | 502/242 |
| 4,403,044 | 9/1983 | Post et al. | 518/714 |
| 4,414,137 | 11/1983 | Young et al. | 502/162 |
| 4,428,862 | 1/1984 | Ward et al. | 502/77 |
| 4,433,187 | 2/1984 | Young | 585/467 |
| 4,443,329 | 4/1984 | Eberly, Jr. et al. | 208/111 |
| 4,495,303 | 1/1985 | Kuehl | 423/329 |

FOREIGN PATENT DOCUMENTS 0035807 9/1981 European Pat. Off.
0070125 1/1983 European Pat. Off.

OTHER PUBLICATIONS

Jeffrey L. Fox, "Zeolites Catalyze Patent Dispute", Science, Jan. 4, 1985, pp. 35-36.
R. von Ballmoos and W. M. Meier, "Zoned Aluminium Distribution in Synthetic Zeolite ZSM-5," Nature, vol. 289, Feb. 26, 1981, pp. 782-783.
Stephen Budiansky, "Research Article Triggers Dispute on Zeolite," Nature, vol. 300, Nov. 25, 1982, p. 309.
Lovat V. C. Reece, "When is a Zeolite Not a Zeolite?," Nature, vol. 296, Apr. 8, 1982, pp. 491-492.
C. A. Fyfe, G. C. Gobbi, J. Klinowski, J. M. Thomas, and S. Ramdas, "Resolving Crystallographically Distinct Tetrahedral Sites in Silicalite and ZSM-5 by Solid-State NMR," Nature, vol. 296, Apr. 8, 1982, pp. 530-533.
D. H. Olsen, W. O. Haag, and R. M. Lago, "Chemical and Physical Properties of the ZSM-5 Substitutional Series," Journal of Catalysis, vol. 61, 1980, pp. 390-396.
E. M. Flanigen, J. M. Bennet, R. W. Grose, J. P. Cohen, R. L. Patton, R. M. Kirchner and J. V. Smith, "Silicalite, a New Hydrophobic Crystalline Silica Molecular Sieve," Nature, vol. 271, No. 5645, Feb. 1978, pp. 512-516.
D. M. Bibby, N. B. Milestone, and L. P. Aldrige, "Silicalite-2, a Silica Analogue of the Aluminosilicate Zeolite ZSM-11," Nature, vol. 280, Aug. 23, 1979.

Primary Examiner—John Doll
Assistant Examiner—Jackson Leeds
Attorney, Agent, or Firm—Cleveland R. Williams; Yale S. Finkle; Dean Sandford

[57] ABSTRACT

A process for producing a thermally shock calcined crystalline silica comprising (A) precalcining a crystalline silica at a relatively low temperature, (B) very rapidly increasing the temperature of the crystalline silica to a relatively high temperature for a short period of time, and (C) rapidly cooling the crystalline silica. The resulting crystalline silica is catalytically active for hydrocarbon conversion reactions and is particularly selective for the production of para-xylene from a reaction mix of toluene and a methylating agent.

24 Claims, No Drawings

SHOCK CALCINED CRYSTALLINE SILICA CATALYSTS

BACKGROUND OF THE INVENTION

1. Field of the Invention

The present invention relates to a crystalline silica and especially to a crystalline silica which is catalytically active and selective in methylation reactions.

2. The Prior Art

A process for selectively producing para-xylene is disclosed in U.S. Pat. No. 4,270,017. Para-xylene is selectively prepared by reacting toluene and a methylating agent in the presence of a phosphorus modified catalyst comprising a silica polymorph intermixed with an inorganic refractory oxide.

U.S. Pat. Nos. 4,325,929 and 4,344,927 relate to a process for hydrothermally preparing a silica polymorph which is described as suitable for use in aromatic alkylation.

U.S. Pat. No. 4,362,653 discloses a catalyst composite comprising a silica polymorph and the use of the catalyst in a hydrocarbon reforming process.

Crystalline silicas and their use as alkylation catalysts are disclosed in U.S. Pat. No. 4,283,306. The patent additionally teaches the use of various promoters combined with the catalysts.

Hydrogenation catalysts are disclosed in U.S. Pat. No. 4,387,258 which relates to palladium or platinum promoters deposited on a low acidity silica polymorph/silicalite/high sillica zeolite.

It is an object of the present invention to provide a crystalline silica for use in catalytically promoting the conversion of hydrocarbons.

Another object of the invention is to provide a catalytically active crystalline silica that is selective for the production of para-xylene.

Yet another object of the invention is to provide a process for the production of para-xylene using catalysts containing said crystalline silica.

Still another object of the invention is to provide a process for producing a crystalline silica.

Other objects and advantages of the invention will be apparent from the following description.

SUMMARY OF INVENTION

The present invention resides in a crystalline silica activated by shock calcination. Typically, the crystalline silica is produced by a method comprising the steps of: (1) precalcining the crystalline silica at a relatively low temperature, (2) rapidly heating the crystalline silica to a relatively high calcination temperature and maintaining the high calcination temperature for a relatively short period of time and (3) rapidly cooling the crystalline silica. When used as a catalyst for hydrocarbon conversion reactions, the crystalline silica is generally combined with a porous refractory oxide and, optionally, with a promoter.

The invention additionally resides in a method of alkylating an aromatic compound which comprises contacting an aromatic compound with a $C_1$ to $C_{10}$ hydrocarbon in the presence of a catalyst comprising a thermally shock calcined crystalline silica.

DETAILED DESCRIPTION OF THE INVENTION

This invention resides in a method for thermally shock calcining crystalline silica and in crystalline silicas activated by such a method, and in catalysts produced therefrom, and in a method of using such catalysts for hydrocarbon conversion reactions, particularly for alkylating an aromatic compound with a $C_1$ to $C_{10}$ hydrocarbon.

Any of the known crystalline silicas may be thermally shock calcined in accordance with the process herein to produce a catalyst which may be used in hydrocarbon conversion reactions.

The preferred crystalline silica composition herein is characterized by pores of uniform diameter of 6 Å or less, and even more preferably 5 Å to 6 Å and is prepared by calcining a crystalline hydrated alkylonium silica prepared by hydrothermal crystallization from a reaction mixture containing as essential reagents, water, amorphous silica and a quarternary ammonium compound, for example, tetraethyl ammonium hydroxide, at a pH of at least 10. The compound thus formed is calcined to decompose the alkylonium moieties present. The crystalline silica exhibits no ion exchange properties; however, because of its uniform pore structue it is capable of making size-selective separations of molecular species.

The crystalline silica produced from the above-described mixture has a topological type of tetrahedral framework, which contains a large fraction of five-membered rings of silica-oxygen tetrahedra. The framework comprises a three-dimensional system of intersecting channels which are defined as ten rings of oxygen atoms extending in three directions. Precursor organic nitrogen ions which occupy the intersecting channels are removed by heating or in the alternative, by extracting with an acid to yield the desired crystalline silica. The resulting void volume occupies approximately 33 percent of the crystal structure, and the three-dimensional channel is wide enough to absorb organic molecules having up to about 6 Å in diameter. The crystalline silicas, herein, degrade to glass products and dense crystalline silica above about 2,732° F.

The crystalline silica employed in this invention is analogous to highly siliceous alkali silicates which form as insoluble compounds during extended hydrothermal digestion. The organic agent, in the form of a nitrogen compound incorporated as a cation during crystallization of the crystalline silicas herein, becomes a source of micropores when eliminated by combustion or extraction. The surface of these micropores are relatively free of hydroxyl groups. The isolated hydroxyl groups which are present provide a moderate acidic strength when the crystalline silica is thermally activated. The crystalline silica is a uniquely, active solid which is suitable for use as a catalyst component or in catalysts used in hydrocarbon reactions.

The crystalline silica provides not only the required surface for the catalyst precursor, but gives physical strength and stability to the catalyst material. In addition, the crystalline silica has a large surface area upon which the catalyst precursor is deposited.

A crystalline silica suitable for use herein is described in U.S. Pat. No. 4,334,927, the disclosure of which is incorporated into this application by reference. The crystalline silica is prepared by hydrothermally crystallizing said crystalline silica from a silicate solution containing an organic agent, in combination with a base solution, and an acid solution. Crystallization is effected utilizing high shear mixing. The crystalline silica has as the four strongest d-values of its x-ray diffraction patern, d=11.05, d=9.96, d=3.82 and d=3.34. The crystalline silica is designated as UCS-3.

Another suitable crystalline silica is described in U.S. Pat. No. 4,325,929, the disclosure of which is incorporated herein by reference. The crystalline silica is prepared in accordance with the procedure of U.S. Pat. No. 4,344,927 above with the following exception: Crystallization is effected by high shear mixing followed by an unagitated period during the crystallization of said silica. The crystalline silica has as the four strongest d-values of its x-ray diffraction pattern, d=10.9, d=4.06, d=3.83 and d=3.33. The crystalline silica is designated as UCS-4.

A particularly preferred crystalline silica suitable for use herein which exhibits molecular sieve properties is termed silicalite. This material has a specific gravity at 25° C. of 1.99±0.05 g/cc as measured by water displacement. After calcination at 600° C. in air for 1 hour, silicalite has a specific gravity of 1.70±0.05 g/cc. The mean refractive index of silicalite crystals measured as the synthesized form is 1.48±0.01, while the calcined form (600° C. in air for 1 hour) is 1.39±0.01.

The x-ray diffraction pattern of silicalite after calcination in air at 600° C. for 1 hour has as its six strongest lines or interplanar spacings d=11.1±0.2, d=10.0±0.2, d=3.85±0.07, d=3.82±0.07, d=3.76±0.05 and d=3.72±0.05.

The pore diameter of silicalite is about 6 Å and its pore volume is 0.18 cc/g as determined by adsorption. The uniform pore structure of silicalite imparts size-selective molecular sieve properties to the composition. These molecular sieve properties permit the separation of p-xylene from o-xylene, m-xylene and ethylbenzene. A more detailed description of silicalite including a method of how to prepare the composition is described in greater detail in U.S. Pat. No. 4,061,724, the disclosure of which is incorporated herein by reference.

The crystalline silicas herein exhibit molecular sieve properties characteristic of certain crystalline aluminosilicate compositions, but exhibit substantially none of the ion-exchange properties which are essential to the aluminosilicates commonly referred to as zeolites. The lack of ion-exchange properties in the crystalline silicas herein is due to the crystal lattice structure of the silicas which does not contain alumina as an integral part of said crystal lattice.

Before the crystalline silica is subjected to thermal shock treatment, the crystalline silica is first precalcined at a temperature of from about 700° F. to about 1,100° F., preferably from about 700° F. to about 900° F. for about 30 minutes to about 2 days. Desirably, the thermal shock calcination of the crystalline silica is conducted at a temperature that is at least 300° F., preferably at least 400° F. higher than the precalcination temperature. Precalcination facilitates a rapid temperature rise during the subsequent thermal shock calcination by decreasing the heat spent in vaporizing water and desorbing volatile components. Additionally, precalcination avoids the formation of aerosols initiated by the rapid evolution of vapors within the crystalline silica aggregates and particles which may cause fragmentation and fluidization of the crystalline silica during subsequent shock calcination of the silica.

After the precalcination treatment, the crystalline silica is subjected to thermal shock calcination. The thermal shock treatment of the crystalline silica may be carried out in steam, air, ammonia, carbon dioxide, carbon monoxide or any inert atmosphere such as nitrogen, hydrogen, flue gas, argon, helium and mixtures thereof, but it is preferably effected in air. In addition, effluent gases from a combustion chamber may be utilized as a source of direct-fired heat. For maximum efficiency in transferring heat through the crystalline silica, the crystalline silica is reduced to a particle size of less than 6 mesh. At or above 7 or 8 mesh, heat transfer becomes a problem and rapid transfer of heat throughout the crystalline silica is difficult to achieve.

During thermal shock calcination, the crystalline silica is subjected to a very rapid increase in temperature wherein the elevated temperature is maintained for a relatively short period of time, because prolonged exposure of the crystalline silica to the relatively high, shock calcination temperature would destroy the original structure of the crystalline silica. Thus, it is critical that the temperature increase very rapidly in the thermal shock calcination of crystalline silicas herein to prevent undesirable fusion and mineralization reactions from occurring. The crystalline silica is heated to a temperature within the range of from about 1,900° F. to about 2,300° F., preferably from about 2,000° F. to about 2,200° F. The crystalline silicas herein are thermally shock calcined by relatively rapidly increasing the temperature to within the range of 1,900° F. to 2,300° F. and maintaining the crystalline silica at temperatures within that range for a relatively short period of time, usually from about 0.1 second to about 20 minutes, preferably from about 0.5 second to about 10 minutes, most preferably from 1 second to about 5 minutes. Preferably the thermal shock calcination temperature is increased at a rate of from about 1° F. per second to about 200,000° F. per second, preferably from about 1° F. per second to about 1,000° F. per second.

One method of rapidly increasing the temperature of the crystalline silica involves contacting a stream of preheated air with a stream of fluidized crystalline silica powder. The crystalline silica powder typically has a particle size of less than 100 microns, preferably from about 6 microns to about 100 microns, most preferably from about 25 microns to about 100 microns, and is fluidized in a flowing gas stream, for example an air stream. A crystalline silica powder having a particle size in this range when mixed with a gas has the characteristics of a fluid when transported through a tube or coil.

A typical apparatus for contacting the air and crystalline silica includes two high-temperature coils connected in series and suspended in a furnace. Air, preheated in the first coil, impinges at a right angle on a stream of fluidized crystalline silica introduced through a tee into the second coil. The crystalline silica is then rapidly cooled, as by introducing a quench stream of cold air into the effluent from the second coil.

Another efficient method of rapidly heating the crystalline silica to the desired temperature is by blending the crystalline silica with a preheated solid silica sand in a sand bath.

Although the invention is not to be held to any particular theory of operation, thermally shock calcining the crystalline silicas herein is believed to alter the crystalline silica surface acidity by the following mechanism: electron-deficient, Lewis-acid sites form when surface hydroxyl groups combine and water is expelled. Crystalline silica surface protonic-acid sites (Bronsted) are eliminated as Lewis-acid sites are formed. The concentration of Lewis-acid sites may decrease as thermal mobility rearranges the crystalline silica surface and the more active acid sites are eliminated. Thus, the thermal shock calcination of the crystalline silicas herein selectively eliminates the strongest acid sites on the crystalline silica surface resulting in a crystalline silica with slightly reduced catalytic activity but greatly enhanced selectivity. Examples of improved catalyst selectivity are the cracking of hydrocarbons to selectively produce higher proportions of intermediate molecular weight products and in alkylation reactions to the selective production of certain isomers, for example, para-xylene in the reaction of toluene with a methylating agent. The optimal thermal shock calcination temperature for the crystalline silica may vary according to the type of crystalline silica, the desired reaction, and the level of activity and selectivity desired.

After the thermal shock calcination step is completed, it is important to rapidly cool the crystalline silica to a temperature of about 1,000° F. or lower. Rapid cooling of the crystalline silica is necessary because crystalline silicas are excellent thermal insulators and retain the high shock calcination temperatures for a period of time sufficient to cause excess sintering and loss of catalytic activity. The thermally shock calcined crystalline silicas may be cooled, for example, by passing the thermally shock calcined crystalline silica through a tube immersed in a water bath or by flowing the crystalline silica particles over an inclined cooled metal plate or through a rotating cooled tube. Another method of rapidly reducing the temperature of the thermally shock calcined crystalline silicas is by quenching the shock calcined crystalline silica is a liquid medium, such as water.

The shock calcination treatment may be performed on the crystalline silica alone, or if the crystalline silica is to be used as a catalyst, in combination with a porous refractory oxide and/or optionally a promoter, then the treatment may be applied to composites containing such components in combination with the crystalline silica. In addition, the crystalline silica treated by shock calcination may be completely or partially cation exchanged, for example, with hydrogen, ammonium, or di- or trivalent metal cations, such as rear earth metal or alkaline earth metal cations for stability purposes or with cations of palladium, platinum, nickel, etc., to provide a hydrogenation component. Other metal cations which may be used herein include chromium, iron, titanium and zirconium.

The crystalline silicas herein may be used alone, in combination with a refractory oxide, in combination with a promoter or in combination with a refractory oxide and a promoter. It should be noted that the use of refractory oxides and promoters herein is optional but preferred.

The crystalline silicas may be mixed with an inorganic refractory oxide in the form of a hydrogel or sol such as peptized boehmite alumina or colloidal silica. The inorganic refractory oxides herein are preferably selected from the group consisting of boehmite alumina, silica hyrdrosol, colloidal silica and mixtures thereof. Other inorganic refractory oxides include alumina, silica, magnesia, beryllia, zirconia and mixtures thereof.

Normally, the crystalline silica and inorganic refractory oxide are mixed in a weight ratio range of from about 1:10 to about 10:1, preferably from about 1:4 to about 4:1.

In order to provide suitable hydrocarbon conversion, hydrodewaxing, desulfurization and denitrogenation activity, the crystalline silicas herein may be composited with a minor amount of a promoter. The amount of promoter incorporated into the final catalyst is typically from about 0.2 to about 35 weight percent, preferably from about 0.5 to about 25 weight percent of the catalyst.

For use in hydroconversion reactions, such as hydrodesulfurization and hydrodenitrogenation processes and hydroconversion processes such as hydrocracking, hydroisomerization, reforming etc., a promoter comprising a hydrogenation component is composited with the crystalline silica catalyst. Effective hydrogenation components comprise the Group IIB, Group VIB, and Group VIII metals as disclosed in the *Periodic Table of Elements*, as published by the Sargent-Welch Scientific Company.

Hydrocarbon conversion reactions such as alkylation, isomerization, transalkylation, etc., may be promoted by compositing the crystalline silica catalyst with one or more promoters selected from the group consisting of the Groups IB, IIA and VA and the rare earth elements of the *Periodic Table of Elements* as above-described and preferably compounds of phosphorus, magnesium, boron, antimony, arsenic and mixtures thereof. One especially preferred alkylation promoter is a phosphorus compound.

Representative phosphorus compounds include derivatives of groups represented by the formulae $PX_3$, $RPX_2$, $R_2PX$, $R_3P$, $X_3PO$, $(XO_3)P$, $R_3P=O$, $R_3P=S$, $RPO_2$, $RPS_2$, $RP(O)(OX)_2$, $RP(S)(SX)_3$, $R_2P(O)OX$, $R_2P(S)SX$, $RP(OX)_2$, $RP(SX)_2$, $ROP(OX)_2$, $RSP(SX)_2$, $(RS)_2PSP(SR)_2$, and $(RO)_2POP(OR)_2$ wherein R is alkyl or aryl and X is hydrogen, alkyl, aryl or halide. These compounds include primary, secondary or tertiary phosphines; tertiary phosphine oxides; tertiary phosphine sulfides; primary and secondary phosphonic acids and their corresponding sulfur derivatives; esters of phosphonic acids; the dialkyl alkyl phosphonates; alkyl dialkyl phosphonates, phosphinous acids, primary, secondary and tertiary phosphites and esters thereof alkyl dialkylphosphinites, dialkyl alkyl-phosphonites their esters and sulfur derivatives.

Other suitable phosphorus-containing compounds include the phosphorus halides such as phosphorus trichloride, phosphorus tribromide, phosphorus triiodide, alkyl phosphorodichlorides, dialkyl phosphorochlorides and dialkyl phosphonochloridites. Preferred phosphorus-containing compounds include phosphoric acid, phosphorus acid, and phosphate esters such as trimethylphosphate, ethylphosphate, ethylphosphite, or monophenylphosphate, etc. and mixtures thereof.

Preferred catalysts for alkylation reactions comprise about 5 to about 30 weight percent phosphorus on a support comprising silica or alumina and a shock calcined silicalite, most preferably in a 1:4 to 4:1 weight ratio.

The alkylation process herein may effectively be carried out by contacting an aromatic hydrocarbon and a $C_1$ to $C_{10}$ hydrocarbon with the above-described crystalline silica under alkylation reaction conditions.

The aromatic hydrocarbon suitable for use preferably is a member selected from the group consisting of benzene, toluene, xylene, ethylbenzene, phenol, and cresol and mixtures thereof. The preferred aromatic hydrocarbon is toluene.

A wide variety of $C_1$ to $C_{10}$ hydrocarbons may be used to alkylate the aromatic hydrocarbons herein. For example, the $C_1$ to $C_{10}$ alkanes, $C_2$ to $C_{10}$ olefins, as well as $C_1$ to $C_{10}$ alicyclic and alkenyl radicals and various methylating agents may be used.

The shock calcined crystalline silicas may be used alone or in combination with refractory oxides and/or promoters for alkylation reactions. In an especially preferred mode, toluene is selectively alkylated to paraxylene by contacting toluene and a methylating agent with a thermally shock calcined crystalline silica. Optionally, the crystalline silica may contain phosphorus or one or more of the other promoters described herein, preferably in conjunction with an inorganic refractory oxide such as alumina, silica, etc. The reaction is carried out at a temperature of from about 700° F. to about 1,150° F., preferably from about 800° F. to about 1,000° F., at a pressure of from about atmospheric pressure to about 250 p.s.i.a., preferably from about 15 p.s.i.a. to about 100 p.s.i.a. The molar ratio of toluene to methylating agent is normally from about 6:1 to about 1:2, preferably from about 3:1 to about 1:1.

Suitable methylating agents include methanol, methylchloride, methylbromide, dimethyl ether, methylcarbonate, dimethylsulfide, etc. The methylation reaction is accomplished using a weight hourly space velocity (WHSV) of from about 1 to 20, especially from about 2 to about 10. Para-xylene is selectively produced in the reaction; however, it should be noted that some ortho-xylene and small amounts of meta-xylene may additionally be produced. Conventional methods may be used to separate the xylene isomers or the undesirable isomers may be converted to para-xylene in an isomerization process. The methylation reaction herein may be carried out as a continuous, semi-continuous or batch type operation, using a fixed or moving type catalyst system utilizing conventional apparatus.

The invention is further illustrated by the following examples which are illustrative of various aspects of the invention and are not intended as limiting the scope of the invention as defined by the appended claims.

EXAMPLE I

A crystalline silica (silicalite) is prepared by mixing 1,100 ml of an alkaline solution containing sodium silicate equivalent to the molar proportions: 100 moles of $SiO_2$, 30 moles of $Na_2O$, and 1,390 moles of water, with 530 ml of an acidic solution containing components equivalent to the molar proportions: 16 moles of NaCl, sulfuric acid equivalent to 21 moles $H_2SO_4$, and 710 moles of water. The resulting gel is mixed with an organic solution containing 59 grams of tri-n-propylamine (n-$C_3H_7$)$_3$, 49 grams of n-propylbromide (n-$C_3H_7Br$) and 94 grams of 2-butanone ($CH_3COC_2H_5$). The resulting mixture is stirred and refluxed 24 hours at 180° F. Next, the vapor space is pressured to 600 p.s.i. with nitrogen and the temperature is increased to 320° F. to 330° F. for 30 hours while stirring at about 200 rpm to form a crystalline silica. The solid product is collected by filtration, washed with distilled water and dried at 240° F.

Next, 1,000 ml of 2.0M ammonium hydrogen sulfate ($NH_4HSO_4$) is prepared by dissolving 132 grams of ammonium sulfate [($NH_4$)$_2SO_4$] in 800 ml of water to form a solution. Next, 28 ml of concentrated sulfuric acid ($H_2SO_4$) is added to the solution and the solution is diluted to 1,000 ml with water.

Then, 300 grams of the silicalite prepared in accordance with the procedure described above is added to the ammonium hydrogen sulfate solution and heated at 170° F. to 200° F. with stirring for one hour. The acid treated silicalite is collected by filtration, washed with barium acetate [$Ba(C_2H_3O_2)_2$] until the filtrate tests sulfate ($SO_4^=$) free and dried at 230° F.

EXAMPLE II

Precalcined 70 wt. % Silicalite Bonded With 30 wt. % Alumina

The dried, acid treated silicalite produced in Example I is blended with Catapal S alumina to form a powder mixture containing 70 wt. % silicalite and 30 wt. % alumina. A combustible porosity promoter equivalent to 10 wt. % of the silicalite composition on a dry weight basis is added to the mixture by blending said mixture with powdered microcrystalline cellulose, manufactured by the FMC Corporation.

The above-described powdered mixture is converted into a paste by mulling with sufficient N/10 nitric acid (as 7 ml of concentrated nitric acid per 1,000 ml solution). Next, the paste is spread into a thin layer, dried at 300° F., calcined at 900° F. for 2 hours, and then granulated into 10/30 mesh aggregates.

EXAMPLE III

Shock Calcined 70 wt. % Silicalite Bonded With 30 wt. % Alumina

A portion of the granules produced in accordance with the procedure of Example II is thermally shock calcined by spreading the granules in ⅛ inch layers in zirconia combustion boats. The boats are placed into a preheated Alundum tube. The average rate of temperature increase for the granules is 2° F./second in the temperature interval of 1,550° F. to 2,160° F. The temperature is held at 2,160° F. to 2,190° F. for 4 minutes. Next, the silicalite-containing catalyst is cooled from 2,190° F. to 1,790° F. at about 1.3° F./second by drawing the catalyst through a ceramic tube and then quenched by dumping on a cold steel plate.

EXAMPLE IV

Shock Calcined 70 wt. % Silicalite Bonded With 30 wt. % Alumina

A shock calcined, silicalite-containing catalyst is prepared in accordance with the procedure of Example III with the following exception:

The average rate of temperature increase is 2° F./second in the temperature interval of 1,550° F. to 2,280° F. and the temperature is held at 2,280° F. to 2,350° F. for 3.25 minutes.

EXAMPLE V

Precalcined 70 wt. % Silicalite Bonded With 30 wt. % Silica

The dried, acid treated silicalite (80 grams) produced in Example I is blended with 1.0 gram of microcrystalline cellulose for 5 minutes. Next, 78 ml of silica and sufficient water are added to the above powdered mixture to form a paste and the resulting mixture is mulled for 5 minutes. Then, the paste is spread into a thin layer, dried at room temperature, granulated into 10/30 mesh aggregates and calcined at 900° F. for 2 hours.

The calcined granules are slurried in 500 ml of 2.0M ammonium nitrate and allowed to stand overnight. The granules are collected, as by filtration, washed twice with distilled water, dried at 230° F. and calcined at 900° F. for 2 hours.

EXAMPLE VI

Shock Calcined 70 wt. % Silicalite Bonded with 30 wt. % Silica

A precalcined, silicalite-containing catalyst is prepared in accordance with the procedure of Example V to produce a shock calcined catalyst with the following exception:

A portion of the granules produced in accordance with the procedure of Example V is thermally shock calcined by spreading the granules in ⅛ inch layers in zirconia combustion boats. The boats are placed into a preheated Alundum tube. The average rate of temperature increase for the granules is 30° F./second. The temperature is held at 2,030° F. for 2 minutes. Next, the silicalite-containing catalyst is quenched by dumping on a cold steel plate.

EXAMPLE VII

Precalcined 10 wt. % $P_2O_5$ on 65 wt. % Silicalite Bonded With 25 wt. % Silica

The dried, acid treated silicalite (26 grams) produced in Example I is blended with 3.5 ml of 85% phosphoric acid and 25 ml of silica to form a mixture and dried at 230° F. The resulting mixture is calcined at 900° F. for two hours and then granulated into 10/30 mesh aggregates. The catalyst contained 10 wt. % phosphorus as $P_2O_5$.

EXAMPLE VIII

Shock Calcined 10 wt. % $P_2O_5$ on 65 wt. % Silicalite Bonded With 25 wt. % Silica

A precalcined, silicalite-containing catalyst is prepared in accordance with the procedure of Example VII to produce a shock calcined catalyst with the following exception:

A portion of the precalcined granules are spread in ⅛ inch layers in zirconia combustion boats. The boats are placed into a preheated Alundum tube. The average rate of temperature increase for the granules is 12° F./second. The temperature is held in the temperature interval of from 2,170° F. to 2,110° F. for 3 minutes. Next, the silicalite-containing catalyst is quenched by dumping on a cold steel plate. It should be noted that after shock calcination, the above-described catalyst contains 8.5 Wt.% phosphorus as $P_2O_5$.

EXAMPLES IX TO XI

Toluene is selectively methylated to para-xylene by feeding a 2:1 molar ratio of toluene and methanol respectively into a reactor containing the crystalline silica catalysts described in Table 1 below. The toluene and methanol are fed into the reactor at atmospheric pressure, a temperature of 1,000° F. and a weight hourly space velocity (WHSV) of 4. The catalysts used and results are described and summarized in Table 1 below:

The above data prove that the catalysts containing the thermally shock calcined crystalline silica (Examples X and XI) are more selective to the production of para-xylene as compared to the otherwise identical catalyst that does not contain a thermally shock calcined crystalline silica (Example IX). Also, the catalysts of Examples X and XI evidence greater selectivity for xylene production than the catalyst of Example IX.

Obviously, many modifications and variations of the invention, as herein before set forth, may be made without departing from the spirit and scope thereof, and only such limitations should be imposed as are indicated in the appended claims.

I claim:

1. A process for treating a microporous crystalline silica which comprises (A) precalcining a microporous crystalline silica at a temperature below the temperature to which the crystalline silica is heated in step (B) but sufficiently high to vaporize water and desorb volatile components, (B) thermally shock calcining the crystalline silica by rapidly increasing the crystalline silica temperature at a rate between about 1° F./second and about 200,000° F./second to a relatively high temperature between about 1900° F. and about 2300° F. and maintaining the high temperature for a period of time between about 0.1 second and about 20 minutes, said period of time being sufficiently short to avoid substantial sintering, and (C) cooling the thermally shock calcined crystalline silica at a rate sufficiently rapid to avoid substantial sintering and substantial loss of catalytic activity from said shock calcining.

2. The process defined in claim 1 wherein the precalcination temperature is about 400° F. or more below the thermal shock calcination temperature.

3. The process defined in claim 1 wherein the microporous crystalline silica is precalcined at a temperature of from about 700° F. to about 1,100° F. for about 30 minutes to about 2 days.

4. The process defined in claim 1 wherein the temperature of the crystalline silica in step (B) is increased to the relatively high temperature at a rate of from about 1° F./second to about 1000° F./second and maintained at the relatively high temperature for about 0.5 second to about 10 minutes.

5. The process defined in claim 1 wherein the crystalline silica is thermally shock calcined by rapidly increasing the crystalline silica temperature to within the range of from about 2000° F. to about 2200° F. and maintaining that temperature for a time between about 1.0 second and about 5 minutes.

6. The process defined in claim 1 wherein the thermally shock calcined crystalline silica is rapidly cooled to a temperature below about 1,000° F.

7. A process for treating a microporous crystalline silica which comprises (A) precalcining a microporous crystalline silica in a temperature range between about 700° F. and about 1100° F., (B) thermally shock calcin-

TABLE 1

| Ex. | Crystalline Silica Catalyst Used | Precalcination °F. | Hrs. | Shock Calcination °F. | Min. | Hours on Stream | Toluene Conversion Wt. % | Selectivity For Xylene Production Wt. % | Xylene Isomers Wt. % | | | Yield P—Isomer Wt. %* |
|---|---|---|---|---|---|---|---|---|---|---|---|---|
| | | | | | | | | | P | M | O | |
| IX | Ex. II | 900 | 2 | — | — | 3 | 25.9 | 87 | 26 | 26 | 25 | 5.9 |
| X | Ex. III | 900 | 2 | 2,160–2,190 | 4 | 3 | 29.4 | 91 | 63 | 22 | 15 | 16.9 |
| XI | Ex. IV | 900 | 2 | 2,280–2,350 | 3.25 | 3 | 18.7 | 93 | 87 | 8 | 5 | 15.1 |

*The yield is calculated as Wt. % P—xylene based on the toluene feed.

ing the crystalline silica by rapidly increasing the temperature of the crystalline silica at a rate of from about 1° F./second to about 1000° F./second to a relatively high temperature range between about 1900° F. and about 2300° F. and maintaining the crystalline silica in said high temperature range for about 0.1 second to about 20 minutes, wherein said crystalline silica is maintained within the relatively high temperature range for a time sufficiently short to avoid substantial sintering and the minimum temperature of the relatively high temperature range is about 400° F. or more above the maximum temperature of the precalcination temperature range, and (C) cooling the thermally shock calcined crystalline silica at a rate sufficiently rapid to avoid substantial sintering and substantial loss of catalytic activity from said shock calcining.

8. The process defined in claim 7 wherein the microporous crystalline silica is precalcined at a temperature in the range of from about 700° F. to about 900° F.

9. The process defined in claim 7 wherein the thermally shock calcined crystalline silica is rapidly cooled below about 1000° F. by passing the thermally shock calcined crystalline silica through a tube immersed in water.

10. The process defined in claim 7 wherein the thermally shock calcined crystalline silica is rapidly cooled in step (C) to a temperature below about 1000° F. by contacting the thermally shock calcined crystalline silica with a stream of cold air.

11. A process for treating a microporous crystalline silica which comprises (A) precalcining a microporous crystalline silica at a temperature of from about 700° F. to about 1100° F. for about 30 minutes to about 2 days, (B) thermally shock calcining the crystalline silica by rapidly increasing the temperature of the crystalline silica at a rate of from about 1° F./second to about 200,000° F./second to a relatively high temperature of from about 1900° F. to about 2300° F. and maintaining the relatively high temperature for about 0.1 second to about 20 minutes, said relatively high temperature being maintained a sufficiently short time to avoid substantial sintering, and (C) cooling the thermally shock calcined crystalline silica at a rate sufficiently rapid to avoid substantial sintering and substantial loss of catalytic activity from said shock calcining.

12. The process defined in claim 11 wherein the microporous crystalline silica is silicalite.

13. The process defined in claim 11 wherein the thermally shock calcined crystalline silica to step (C) is rapidly cooled to a temperature below about 1000° F. by flowing the the thermally shock calcined crystalline silica over an inclined, cooled metal plate.

14. A process for treating a microporous crystalline silica which comprises (A) precalcining a microporous crystalline silica at a temperature of from about 700° F. to about 1100° F., (B) thermally shock calcining the crystalline silica by rapidly increasing the temperature of the crystalline silica at a rate of about 1° F./second to about 1000° F./second to a relatively high temperature of from about 1900° F. to about about 2300° F. and maintaining said relatively high temperature for a period of time between about 0.1 second and about 20 minutes, said peiord of time being sufficiently short to avoid substantial sintering, and (C) cooling the thermally shock calcined crystalline silica at a rate sufficiently rapid to avoid substantial sintering and substantial loss of catalytic activity from said shock calcining.

15. The process defined in claim 14 wherein the microporous crystalline silica is precalcined for about 30 minutes to about 2 days.

16. The process defined in claim 14 wherein the thermally shocked calcined crystalline silica is rapidly cooled to a temperature below about 1000° F. by passing the thermally shock calcined crystalline silica through a rotating cooled tube.

17. A crystalline silica produced by the method of (A) precalcining a microporous crystalline silica at a temperature below the temperature to which the crystalline silica is heated in step (B) but sufficiently high to vaporize water and desorb volatile components, (B) thermally shock calcining the microporous crystalline silica by rapidly increasing the crystalline silica temperature at a rate between about 1° F./second and about 200,000° F./second to a relatively high temperature between about 1900° F. and about 2300° F. and maintaining said relatively high temperature for about 0.1 second to about 20 minutes, wherein said relatively high temperature is maintained for a sufficiently short time to avoid substantial sintering, and (C) cooling the thermally shock calcined microporous crystalline silica at a rate sufficiently rapid to avoid substantial sintering and substantial loss of catalytic activity from said shock calcining.

18. A crystalline silica produced by the method of (A) precalcining silicalite at a temperature below the temperature to which the silicalite is heated in step (B) but sufficiently high to vaporize water and desorb volatile components, (B) thermally shock calcining the silicalite by rapidly increasing the silicalite temperature at a rate between about 1° F./second and about 200,000° F./second to a relatively high temperature between about 1900° F. and about 2300° F. and maintaining said relatively high temperature for about 0.1 second to about 20 minutes, wherein said relatively high temperature is maintained for a sufficiently short time to avoid substantial sintering, and (C) cooling the thermally shock calcined silicalite at a rate sufficiently rapid to avoid substantial sintering and substantial loss of catalytic activity from said shock calcining.

19. The crystalline silica defined in claim 17 wherein the microporous crystalline silica is precalcined at a temperature between about 700° F. and about 1100° F.

20. The crystalline silica defined in claim 19 wherein the thermally shock calcined microporous crystalline silica is rapidly cooled to a temperature below about 1000° F. by flowing the thermally shock calcined microporous crystalline silica over an inclined, cooled metal plate.

21. The crystalline silica defined in claim 19 wherein the thermally shock calcined microporous crystalline silica is rapidly cooled to a temperature below about 1000° F. by contacting the thermally shock calcined microporous crystalline silica with a stream of cold air.

22. The crystalline silica defined in claim 19 wherein the thermally shock calcined microporous crystalline silica is rapidly cooled to a temperature below about 1000° F. by quenching the thermally shock calcined microporous crystalline silica in a liquid medium.

23. The crystalline silica defined in claim 18 wherein the silicalite is precalcined at a temperature between about 700° F. and about 1100° F.

24. The crystalline silica defined in claim 23 wherein the thermally shock calcined silicalite is rapidly cooled to a temperature below about 1000° F.

* * * * *

UNITED STATES PATENT AND TRADEMARK OFFICE
CERTIFICATE OF CORRECTION

PATENT NO. : 4,582,694

DATED : 04/15/86

INVENTOR(S) : Dean A. Young

It is certified that error appears in the above-identified patent and that said Letters Patent are hereby corrected as shown below:

Col. 2, line 21, delete "structue" and insert therefor --structure--.

Col. 5, line 42, delete "rear" and insert therefor --rare--.

Col. 5, line 59, delete "hyrdrosol" and insert therefor --hydrosol--.

Line 7 of Table 1 delete "IX   Ex. II   900   2   -   -   3   25.9   87   26   26   25   5.9" and insert therefor --IX   Ex. II   900   2   -   -   3   25.9   87   26   49   25   5.9--.

Signed and Sealed this

Seventeenth Day of November, 1987

Attest:

DONALD J. QUIGG

Attesting Officer

Commissioner of Patents and Trademarks